United States Patent [19]

Fleer et al.

[11] Patent Number: 5,646,012
[45] Date of Patent: Jul. 8, 1997

[54] YEAST PROMOTER AND USE THEREOF

[75] Inventors: Reinhard Fleer, Bures Sur Yvette; Alain Fournier, Chatenay Malabry; Jean-Francois Mayaux, Fontenay aux Roses; Patrice Yeh, Paris, all of France

[73] Assignee: Rhone-Poulenc Rorer S.A., Antony, France

[21] Appl. No.: 483,639

[22] Filed: Jun. 7, 1995

Related U.S. Application Data

[63] Continuation of Ser. No. 140,093, filed as PCT/FR92/00375 Apr. 28, 1992, abandoned.

[30] Foreign Application Priority Data

Apr. 30, 1991 [FR] France ................... 91 05294

[51] Int. Cl.$^6$ ................ C12P 21/02; C12N 1/19; C12N 15/81; C07K 19/765
[52] U.S. Cl. ................ 435/69.1; 435/254.2; 435/320.1; 435/172.3; 530/263; 536/25.5; 536/24.1
[58] Field of Search ................ 536/24.1, 23.5; 435/69.1, 172.3, 71.1, 320.1, 254.2; 530/363

[56] References Cited

PUBLICATIONS

Nucleic Acids Res. 10(8):2625–2637, 1982, Dobson, Kingsman, Tuite, Kingsman, & Roberts, Conservation of high efficiency promoter sequences in Saccharomyces cerevisiae.

Nucleic Acids Res. 18(2)365, 1990, Fournier, Fleer, Yeh, & Mayaux, The primary structure of the 3–phosphoglycerate kinase (PGK) gene from Kluyveromyces–lactis.

Bio/Technology 8:135–139, 1990, van der Berg, van der Laken, van Ooyen, Renniers, Rietveld et al. Kluyveromyces as a Host for Heterologous Gene Expression: Expression and Secretion of Prochymosin.

Nucleic Acids Res. 10(23):7791–7808, 1982, Hitzeman, Hagie, Hayflick, Chen, Seeburg & Derynck The Primary Structure of the Saccharomyces cerevisiae gene for 3–phosphoglycerate kinase.

Mol. Cell Biol. 9(7):3058–3072, 1989, Linton, Yen, Selby, Chen, Chinsky et al. Dual Bidirectional Promoters at the Mouse dhfr Locus: Cloning and Characterization of two messenger RNA Classes of the divergently transcribed rep–1 gene.

EP 0361991 filed Aug. 9, 1989, issued Apr. 4, 1990, Fleer, Fukuhara & Yeh, Method for the microbiological preparation of human serum albumin and other proteins in yeast.

*Primary Examiner*—Nancy T. Vogel

[57] ABSTRACT

The present invention concerns DNA sequences from the *K. lactis* PGK gene having transcriptional promoter activity, to expression vectors comprising these sequences and to their use for the production of proteins.

23 Claims, 14 Drawing Sheets

```
       10         20         30         40         50         60
TCTAGATTTA GCGGGTCATC GAAATTTAGT AGCGAGTCTA TTAGGGACCA GAGTTGCAAC 70         80         90        100        110        120
CTGAGCTTTA ATGCGTCATC CTGTCGTTGC TTCAAGTTCC CCACTTGAAT CACTTGGACA 130        140        150        160        170        180
AACCGTTTCA TTGGTTTGAG GAAGGTGACG GATCTGGGTA GAAACTGGAC TACTGCATCT 190        200        210        220        230        240
GTTGGTAGTC TTGATGCCAT GGTGATGAGC CATTGCCATT GGAAAAGAGT GAATTCAGAT 250        260        270        280        290        300
TCCAAGATTT GGTCAATGAT TGATTTTGTA AGATTGAGAT CGTAATCCTG ATACTCTTTG 310        320        330        340        350        360
AGCCATGTTT CCAACAGTTC TTCGGAATCT GCCGGTGTGG AAACGAGTAT TTCGGAGTAC 370        380        390        400        410        420
AATCTCGGTG GTTGCGTTAT CTGAGAGGAT GGTGTAGTGG TTTGATGTTG CTGTGTGAAA 430        440        450        460        470        480
GATGATGCAG AGCTGATCAA CGATTCGAAC TGGGAGATCA CTTCGTTCAC TTCTTCCTGG 490        500        510        520        530        540
TTCCCGTTAC CTGTTTGCGT TTCCTCATAC ATTGGTACGC TATCCTCATC TTCAGATAAC 550        560        570        580        590        600
GAAATATCAA ACTCATCGGA ATCGGACGCG TCGTTCAAAT CGCCCTCATC CTTGGTAATG 610        620        630        640        650        660
TTCTTGAACC GGTCGAGAAG GTTGAGAATC TCTGTCGGAA CACCACCCTG CGGCGTATAC 670        680        690        700        710        720
CAGAACCAGA ATAAATTGTA GCACATCTTA ACTTTCTCTA AGGAAACATC TGAACTCTGA 730        740        750        760        770        780
TCAACGCATT CCGTAAGTAT ACTGTTTGCC TTGTCTCTGG TGAATTTATG AGGGTAAGAC 790        800        810        820        830        840
TCTGAGATCA TAAGTAACTG TTGAGCATCG AAGTTGTTGT AGTTTGAAAT TAGGGATCTG 850        860        870        880        890        900
GAAAGATGCG GTACCACTGC TTTGATGACA TTATCTGGCG GGTTCAACGG TACCAATTCC 910        920        930        940        950        960
TGCAAGAATA GCGAATCCAA CGGTTTTAAC TCAGAGTAAT GGTTGATCAA CTCGATGAAA 970        980        990       1000       1010       1020
ACGTCCCAAT GGATGGATTG CATCAAGTGT TGATGTTCCA CCAAATTAAG ACAATATTTC 1030       1040       1050       1060       1070       1080
GTAACGTTTT CGAGTGAAAC TGACACGGGC CTGCCCTCAG CACTCGTAGA CACGAGTAAC 1090       1100       1110       1120       1130       1140
GTCTTGAGAC CTCTCGTACA GGGAAGCGAC ATATCGTTCA ATAGACTATG GAACAAAGTG 1150       1160       1170       1180       1190       1200
TACACCGCAG CGATATCCTT GCATTTGCAA AACGATTGAA TAAGTGACGT CGATGCTAAA 1210       1220       1230       1240       1250       1260
TCCTGGATAA GTACGCTGGT ATCGTGTAAG CCCATGAGAA CGACACGTTC CTCATCACTA
```

FIG. 1A        [SEQ ID NO: 1]

```
        1270       1280       1290       1300       1310       1320
   GAAGCCGAAC TGTTGTCTTC AGTGGGGATT GGTTCGACAT TTTGCCAATT GCTGTCGATG 1330       1340       1350       1360       1370       1380
   TACCCTTTCA AAGCCATGTA CCTTAAATCT TCATCCTTGG CAAGTAGATT CATCGGGTGT 1390       1400       1410       1420       1430       1440
   GTTTGAAGTA AGAATATTTG CTTGTTTTA TGGTATCAAA GGTATATGTT GTAGAAGACA 1450       1460       1470       1480       1490       1500
   ATTTCCGGTA ATCCAATTGT CTGTCTGCTC AGTTTAGCAC ATGTATAGTA CGTTGCACAT 1510       1520       1530       1540       1550       1560
   AGTCTACAAT ATTCAGCATT CAGCATTCAG TATACAGCAT ATGGCTAAAT GATCACAAAT 1570       1580       1590       1600       1610       1620
   GTGATTGATG ATTTGACACG ACTAGAAAAG AGAACGAAAA AGGGAAATTC ATGTCACGTC 1630       1640       1650       1660       1670       1680
   CGTTGGCACG TGACATGGAA TATCGAAGAA AGAAAAAAAA AAACGATCTC GTCCTAGTGG 1690       1700       1710       1720       1730       1740
   AAGCCCAGAG TCTGGTCCCC CCGGAGTCTT CCCAAAACAA GAAGCTGACA CATGTTGACA 1750       1760       1770       1780       1790       1800
   CAGAACACCC CACAGCAAAT GCACCACGCT ACGTAGATCA GGAAGCTTAA CTCTAGCGAC 1810       1820       1830       1840       1850       1860
   CTGTCGCTCG CCCCACAGAA CCTCACCCGA GAACCACACA TTACACGCCG CCAGCTCCCA 1870       1880       1890       1900       1910       1920
   CTATACTCAT CTTGCTTCCC TTAAGCGTTC TCACGATTCG TTCGCTGCCC TTCTTCAAGA 1930       1940       1950       1960       1970       1980
   GTCTTCTGAT TCTAATTCTC ATTCGAAATC CTCTACAGTT AATGAATTGC TTGACATGAC 1990       2000       2010       2020       2030       2040
   ATTCATTGTC TCATGGTTTT GGCTTTTGG CTTTTGTCTT TTAAAGCTAT ATCAACTTTA 2050       2060       2070       2080       2090       2100
   CATATAAATA TACGTCAAAA GGGGATTCAT TAATTAGAAA ATTCTCTTTT TCAATAGTTG 2110       2120       2130       2140       2150       2160
   CTATTCATTA TCAATCTATT CAACTCAATT GGTTATTATT TTCATCTTTT TGTCATCCTA 2170       2180       2190       2200       2210       2220
   AACCATCAAC AATATTTAAA TATATCTGTT GCTACATTAA GAGTTACTTC AGAAATAACA 2230       2240       2250
   AAAAAATCGA TCAAGAATTA ATAAAAATG
                                Met                     [SEQ ID NO: 1]
```

FIG. 1B

Oligodeoxynucleotide A
5'CAT GTCGAC TTTTTATTAATTCTTGATCGAT3' [SEQ ID NO: 5]
     SalI
Oligodeoxynucleotide B                [SEQ ID NO: 6]
5'ATG AAGCTT AAATCTTCATCCTTGGC3'
     HindIII
Oligodeoxynucleotide C
5'GGGTGAGGTTCTGTGGGGCGAGCGACAGGTCGCTAGAGTTAAGCATCCTGATC3'
(Position: 439 to 492)                [SEQ ID NO: 7]

Oligodeoxynucleotide D
5'GATCAGGATGCTTAACTCTAGCGACCTGTCGCTCGCCCCACAGAACCTCACCC3'
(Position: 439 to 492)                [SEQ ID NO: 8]

```
HindIII    10         20         30         40         50         60
aagcttTTAA ATCTTCATCC TTGGCAAGTA GATTCATCGG GTGTGTTTGA AGTAAGAATA  60
ttcgaaAATT TAGAAGTAGG AACCGTTCAT CTAAGTAGCC CACACAAACT TCATTCTTAT TTTGCTTGTT TTTATGGTAT CAAAGGTATA TGTTGTAGAA GACAATTTCC GGTAATCCAA 120
AAACGAACAA AAATACCATA GTTTCCATAT ACAACATCTT CTGTTAAAGG CCATTAGGTT TTGTCTGTCT GCTCAGTTTA GCACATGTAT AGTACGTTGC ACATAGTCTA CAATATTCAG 180
AACAGACAGA CGAGTCAAAT CGTGTACATA TCATGCAACG TGTATCAGAT GTTATAAGTC CATTCAGCAT TCAGTATACA GCATATGGCT AAATGATCAC AAATGTGATT GATGATTTGA 240
GTAAGTCGTA AGTCATATGT CGTATACCGA TTTACTAGTG TTTACACTAA CTACTAAACA CACGACTAGA AAAGAGAACG AAAAAGGGAA ATTCATGTCA CGTGCGTTGG CACGTGACAT 300
GTGCTGATCT TTTCTCTTGC TTTTTCCCTT TAAGTACAGT GCACGCAACC GTGCACTGTA GGAATATCGA AGAAAGAAAA AAAAAAACGA TCTCGTCCTA GTGGAAGCCC AGAGTCTGGT 360
CCTTATAGCT TCTTTCTTTT TTTTTTTGCT AGAGCAGGAT CACCTTCGGG TCTCAGACCA CCCCCCGGAG TCTTCCCAAA ACAAGAAGCT GACACATGTT GACACAGAAC ACCCCACAGC 420
GGGGGGCCTC AGAAGGGTTT TGTTCTTCGA CTGTGTACAA CTGTGTCTTG TGGGGTGTCG AAATGCACCA CGCTACGTAG ATCAGGATGC TTAACTCTAG CGACCTGTCG CTCGCCCCAC 480
TTTACGTGGT GCGATGCATC TAGTCCTACG AATTGAGATC GCTGGACAGC GAGCGGGGTG AGAACCTCAC CCGAGAACCA CACATTACAC GCCGCCAGCT CCCACTATAC TCATCTTGCT 540
TCTTGGAGTG GGCTCTTGGT GTGTAATGTG CGGCGGTCGA GGGTGATATG AGTAGAACGA TCCCTTAAGC GTTCTCACGA TTCGTTCGCT GCCCTTCTTC AAGAGTCTTC TGATTCTAAT 600
AGGGAATTCG CAAGAGTGCT AAGCAAGCGA CGGGAAGAAG TTCTCAGAAG ACTAAGATTA TCTCATTCGA AATCCTCTAC AGTTAATGAA TTGCTTGACA TGACATTCAT TGTCTCATGG 660
AGAGTAAGCT TTAGGAGATG TCAATTACTT AACGAACTGT ACTGTAAGTA ACAGAGTACC TTTTGGCTTT TTGGCTTTTG TCTTTTAAAG CTATATCAAC TTTACATATA AATATACGTC 720
AAAACCGAAA AACCGAAAAC AGAAAATTTC GATATAGTTG AAATGTATAT TTATATGCAG AAAAGGGGAT TCATTAATTA GAAAATTCTC TTTTTCAATA GTTGCTATTC ATTATCAATC 780
TTTTCCCCTA AGTAATTAAT CTTTTAAGAG AAAAAGTTAT CAACGATAAG TAATAGTTAG TATTCAACTC AATTGGTTAT TATTTTCATC TTTTTGTCAT CCTAAACCAT CAACAATATT 840
ATAAGTTGAG TTAACCAATA ATAAAAGTAG AAAAACAGTA GGATTTGGTA GTTGTTATAA TAAATATATC TGTTGCTACA TTAAGAGTTA CTTCAGAAAT AACAAAAAAA TCGATCAAGA 900
ATTTATATAG ACAACGATGT AATTCTCAAT GAAGTCTTTA TTGTTTTTTT AGCTAGTTCT ATTAATAAAA Agtcgac                                                 917
TAATTATTTT Tcagctg
     10    SalI 20        30         40         50         60
                     [SEQ ID NO: 2]
```

FIG. 6

YEAST PROMOTER AND USE THEREOF

This is a continuation of application Ser. No. 08/140,093 filed on Nov. 1, 1993, abandoned, which is a national stage application filed under 35 U.S.C.371 of PCT/FR92/00375 filed Apr. 28, 1992.

The present invention relates to the field of molecular biology. More particularly, it relates to a novel DNA sequence having a transcriptional promoter activity, to expression vectors containing this sequence and to the use thereof for the production of proteins, for example heterologous proteins. The invention also relates to recombinant cells containing this DNA sequence.

The progress accomplished in the field of molecular biology has enabled microorganisms to be modified in order to make them produce heterologous proteins. In particular, many genetic studies have been carried out on the bacterium *E. coli*. However, the industrial application of these novel modes of production is still limited, in particular by problems of efficiency of gene expression in these recombinant microorganisms. Accordingly, research studies have been carried out with the aim of increasing the efficiency of these production systems in order to isolate strong promoters enabling high levels of expression of heterologous proteins to be obtained. In *E. coli*, the tryptophan operon and the lactose operon promoters may be mentioned in particular.

More recently, in the yeast *S. cerevisiae*, studies have been carried out on promoters derived from genes involved in glycolysis. There may be mentioned in particular the work on the promoter of the 3-phosphoglycerate kinase PGK gene (Dobson et al., Nucleic Acids Res. 10:2625, 1982; Hitzeman et al., Nucleic Acids Research 10:7791, 1982), the glyceraldehyde-3-phosphate dehydrogenase GAPDH gene (Holland et al., J. Biol. Chem. 254:9839, 1979; Musti et al., Gene 25:133, 1983), the alcohol dehydrogenase 1 ADH1 gene (Bennentzen et al., J. Biol. Chem. 257:3018, 1982; Denis et al., J. Biol. Chem. 25:1165, 1983), and the enolase 1 ENO1 gene (Uemura et al., Gene 45:65, 1986).

Recently, genetic tools have been developed in order to make use of the yeast Kluyveromyces as a host cell for the production of recombinant proteins. The discovery of a 2-micron type plasmid derived from *K. drosophilarum* (plasmid pKD1; described in European Patent No. 241,435) has enabled a very efficient host/vector system for the production of recombinant proteins (EP 361,991) to be established. However, the promoters used in this system have never been optimized. In particular, the promoters involved are essentially heterologous promoters, that is to say derived from other microorganisms, such as *S. cerevisiae*. This situation may lead to various disadvantages. The activity of the promoter may be limited because of the absence of certain elements of the transcriptional machinery (for example, trans-activators). A certain toxicity to the host cell may occur due to an absence of regulation, or the stability of the vector may be affected.

Under these conditions, the lack of strong homologous promoters in Kluyveromyces constitutes a limiting factor in the industrial exploitation of this expression system.

The Applicant has now identified, cloned and sequenced a region of the *Kluyveromyces lactis* genome having transcriptional promoter activity (see FIG. 1 [SEQ ID NO: 1]). More specifically, this region corresponds to the promoter of the *K. lactis* PGK gene. This region, or derivatives or fragments thereof, may be used for the efficient production of recombinant proteins in yeasts of the Kluyveromyces genus. It is understood that this sequence may also be used in other host organisms.

Moreover, an analysis of the region of the Kluyveromyces genome obtained has identified two reading frames in the two opposite directions (see FIG. 2). This observation shows that the complementary strand of the region presented in FIG. 1 also possesses a promoter activity acting in the other direction.

One subject of the present invention therefore lies in a DNA sequence comprising all or part of the sequence presented in FIG. 1 [SEQ ID NO: 1], or a sequence of its complementary strand, or of a derivative of these, and possessing promoter activity.

Within the context of the present invention, derivative is understood to mean any sequence obtained from the sequence given in FIG. 1 [SEQ ID NO: 1], by structural modifications (mutations, deletions, substitutions, additions, restrictions and the like) which conserve promoter activity. In particular, the mutations may involve one or more nucleotides, and the additions and/or substitutions may involve regulatory elements or activator regions such as UASs.

When a derivative is produced, its transcriptional promoter activity may be demonstrated in several ways and in particular by placing a resistance gene or a complementation marker under the control of the sequence studied. Other techniques known to a person skilled in the art may obviously be used to this effect.

A more specific subject of the invention relates to a DNA sequence corresponding to the region between the 2 open reading frames ORF PGK and ORF X, as presented in FIG. 6 [SEQ ID NO: 2].

Another subject of the invention relates to a recombinant DNA comprising a DNA sequence as defined above.

This recombinant DNA may contain, for example, the promoter sequence presented in FIG. 1 [SEQ ID NO: 1] or a derivative thereof, in which a restriction site is inserted, facilitating the use of this sequence as "portable" promoter.

Preferably, this recombinant DNA contains, in addition, one or more structural genes.

Still more preferably, the recombinant DNA also contains signals permitting the secretion of the expression product of said structural gene(s).

In a specific embodiment of the invention, the recombinant DNA is part of an expression plasmid which may be autonomously replicating or integrative in nature.

In particular, autonomously replicating vectors may be obtained by using autonomously replicating sequences (ARS) in the host selected. In yeast in particular, replication origins derived from known plasmids (pKD1, 2μ, and the like) may be involved.

Integrative vectors may be obtained in particular by using homologous sequences at certain regions of the host genome which permit integration of the vector by homologous recombination.

The sequence presented in FIG. 1 was obtained by screening a total genomic DNA library from *Kluyveromyces lactis* by means of a heterologous probe derived from the *S. cerevisiae* PGK gene. The Applicant has indeed shown that it is possible to clone a promoter region in Kluyveromyces, by hybridization using heterologous probes corresponding to a *S. cerevisiae* gene. Details of the cloning of the sequence are given in the examples. The intergenic region may then be isolated from this sequence, in particular by restriction site insertion using the PCR amplification technique, as indicated in the examples.

Another subject of the invention relates to the recombinant cells which contain a DNA sequence as defined above.

Advantageously, cells are chosen from yeasts, and still more preferably from yeasts of the Kluyveromyces genus. It is understood, however, that the invention covers all the recombinant cells in which the promoter regions of the invention are active.

These cells may be obtained by any method enabling a foreign DNA to be introduced into a cell. The methods involved may be in particular transformation, electroporation or any other technique known to a person skilled in the art.

Another subject of the invention relates to the use of a sequence as defined above, for the expression of recombinant genes.

As illustrated by the examples, the DNA sequences according to the invention indeed permit high levels of production of recombinant proteins.

Moreover, the bi-directional promoter activity of the sequences of the invention permits a particularly advantageous use. In particular, it is possible to use these sequences in the 2 directions possible, for the simultaneous expression of several structural genes.

Advantageously, the invention relates to the use of a sequence as defined above for the simultaneous expression of recombinant genes in the 2 opposite directions.

Advantageously, the sequences of the invention may be used for the expression of genes encoding proteins of interest in the pharmaceutical or foodstuffs sectors. By way of example, there may be mentioned enzymes (such as in particular superoxide dismutase, catalase, amylases, lipases, amidases, chymosin and the like), blood derivatives (such as serum albumin, alpha- or beta-globin, factor VIII, factor IX, von Willebrand factor, fibronectin, alpha-1-antitrypsin and the like), insulin and its variants, lymphokines (such as interleukins, interferons, colony stimulating factors (G—CSF, GM—CSF, M—CSF and the like), TNF, TRF and the like), growth factors (such as growth hormones, erythropoietin, FGF, EGF, PDGF, TGF and the like), apolipoproteins, antigenic polypeptides for the production of vaccines (hepatitis, cytomegalovirus, Epstein-Barr, herpes and the like) or alternatively polypeptide fusions such as in particular fusions comprising an active part fused with a stabilizing part (for example fusions between albumin or fragments of albumin and the virus receptor or part of a virus receptor (CD4, and the like)).

The invention will be more completely described by means of the examples which should be considered as illustrative and nonlimiting. Other and further objects, features, and advantages will be apparent from the following description of the preferred embodiments of the invention given for the purpose of disclosure when taken in conjunction with the following drawings.

BRIEF DESCRIPTION OF THE FIGURES

FIG. 1: Nucleotide sequence of the 2.2 kb region of the chromosomal fragment situated upstream of the initiation codon for translation of the K. lactis PGK gene having the promoter activity [SEQ ID NO: 1].

FIG. 6: Nucleotide sequence of the intergenic region of the 2.2 kb fragment. 6(a): oligodeoxynucleotides used in the PCR reactions [SEQ ID NOS: 5–8]. 6(b): SalI—HindIII fragment corresponding to the nucleotides 1343 to 2246 on the sequence in FIG. 1 [SEQ ID NO: 2].

EXAMPLES

The following examples describe the isolation and use of the promoter of the present invention and are not intended to be limiting unless so expressly stated.

Example 1

Isolation of the Promoter Region of the K. lactis PGK Gene

The sequence presented in FIG. 1 was obtained by screening a total genomic DNA library from Kluyveromyces lactis CBS2359 using a heterologous probe derived from the S. Cerevisiae PGK gene (Dobson et al., Nucleic Acids Res. 10:2625, 1982). More specifically, the probe used corresponds to the 1.3 kb N-terminal PvuI-EcoRI fragment of the S. Cerevisiae PGK gene.

In Southern blotting (Southern et al., J. Biol. Chem. 98:503, 1975), the probe used hybridizes to two different fragments when the genomic DNA is digested with XbaI. One fragment, of about 2.5 kb, was isolated by screening a small genomic library from K. lactis CBS2359 consisting of XbaI-cut DNA fragments of between 2 and 3 kb in size, which were introduced inside the plasmid pUC18 at the XbaI site. A library with 500 clones was thus produced and then screened with the heterologous probe described above.

Figure 3:
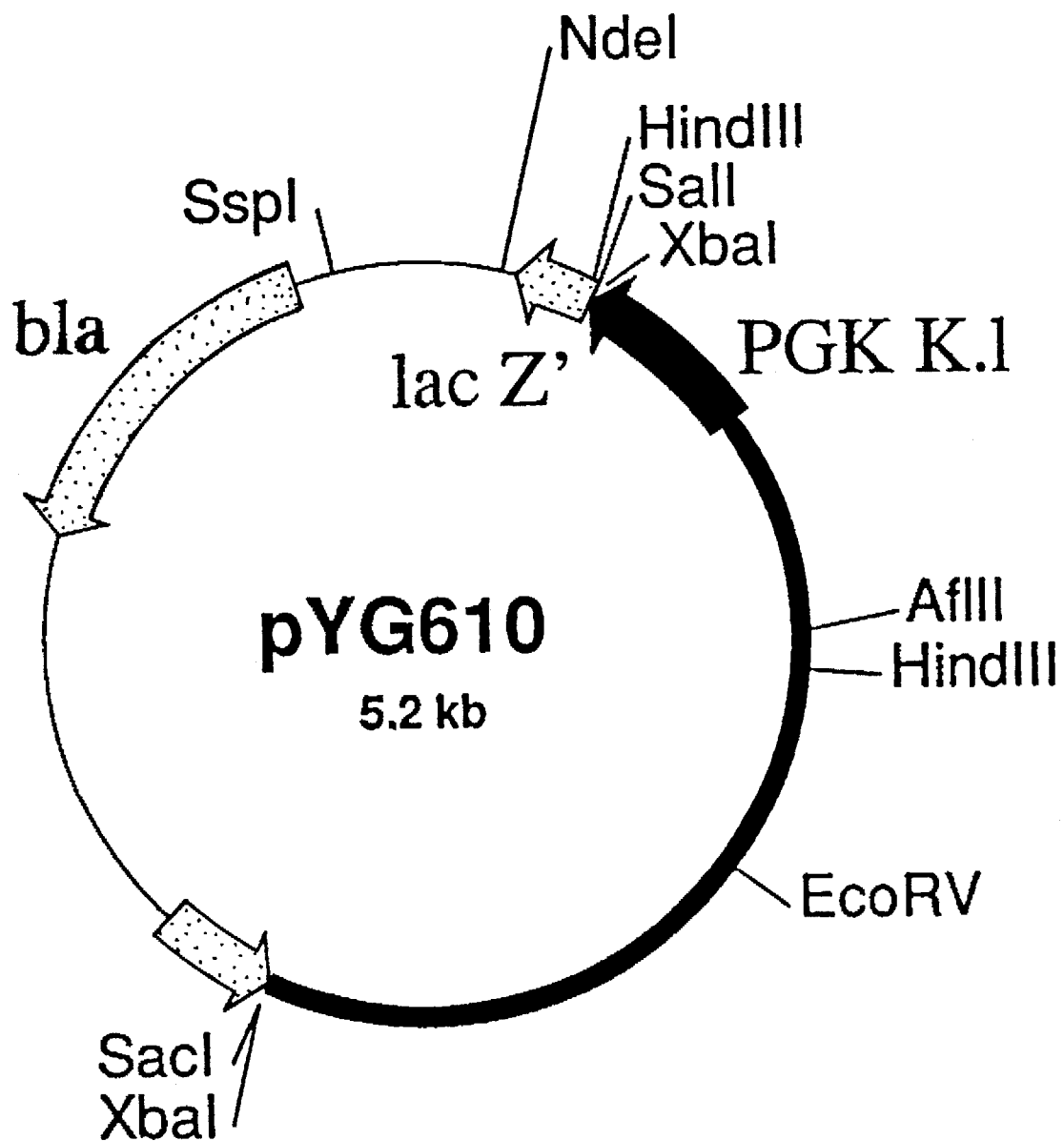
FIG. 3: Restriction map of the plasmid pYG610. The black region corresponds to the region isolated from the K. lactis genome.

A clone was identified by colony hybridization and its plasmid DNA was prepared. This plasmid (pYG610) contains a 2.5 kb genomic DNA fragment whose restriction map is presented in FIG. 3. The plasmid pYG611 contains the same insert in the opposite direction (see FIG. 8).

Figure 4:
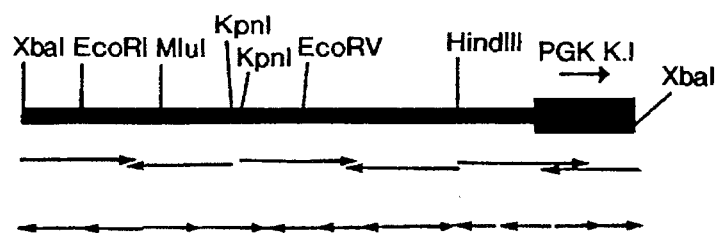
FIG. 4: Strategy for sequencing the 2.5 kb XbaI fragment.

In a second stage, the 2.5 kb fragment thus isolated was sequenced using the Sanger method (Sanger et al., Proc. Nat. Acad. Sci USA 74:5463, 1977). For that, the fragment derived from pYG611 was first subcloned in the bacteriophages M13tg130 and M13tg131. The strategy for the sequencing of the fragment is schematically represented in FIG. 4.

Figure 2:
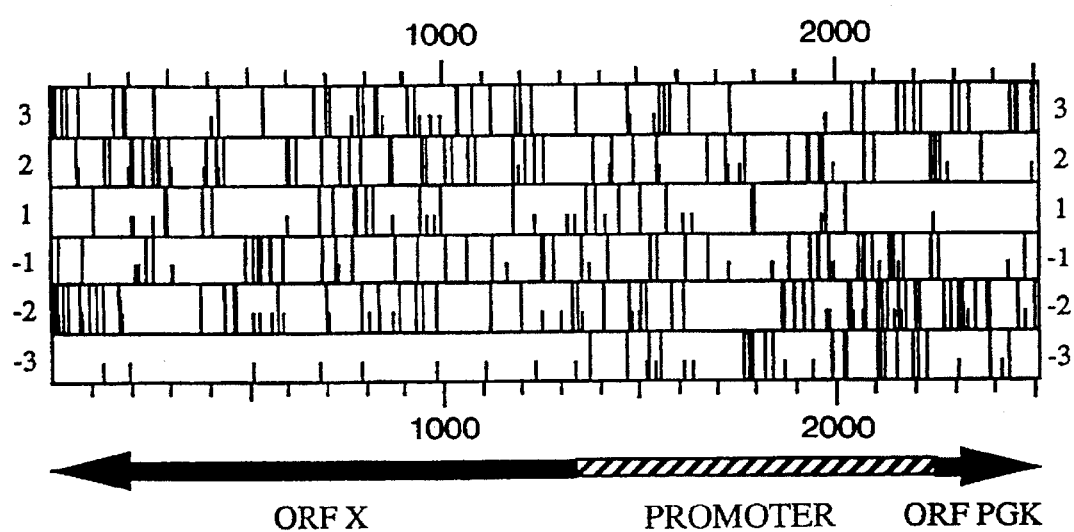
FIG. 2: Analysis of the open reading frames. The 6 possible reading frames are shown ad −3, −2, −1, 1, 2, 3. The vertical half-lines represent translation initiation codons. The full vertical lines represent stop codons. The clear regions show the open reading frames (ORF X and ORF PGK).

Analysis of the sequence obtained showed that the fragment isolated contains a part encoding the N-terminal region of the protein PGK from *Kluyveromyces lactis* (0.3 kb), and 2.2 kb corresponding to the promoter region situated upstream of the site of initiation of translation. It shows furthermore that a second reading frame, situated about 0.9 kb upstream of the ATG of the PGK gene, is situated in the opposite direction relative to the PGK gene (FIG. 2).

Comparison of this sequence with that of the promoter of the *S. Cerevisiae* PGK gene reveals the absence of specific homology, especially with its regulatory element. This sequence therefore corresponds to a completely novel promoter region, which is very distinct from those previously described, from the point of view of its structure and consequently from the point of view of its regulation.

Example 2

Construction of Expression Vectors for the Production of Heterologous Proteins

This example illustrates the use of the promoter capabilities of the 2.2 kb sequence of the sequence in FIG. 1 [SEQ ID NO: 1] and of derived sequences.

a) Insertion of a restriction site at position −6 relative to the ATG

The insertion of this site subsequently enables any gene which is to be expressed to be introduced downstream of the promoter. For reasons of compatibility with existing expression vectors (EP 361,991 ), "portable" promoters were constructed in the form of SalI—HindIII fragments.

Figure 5:
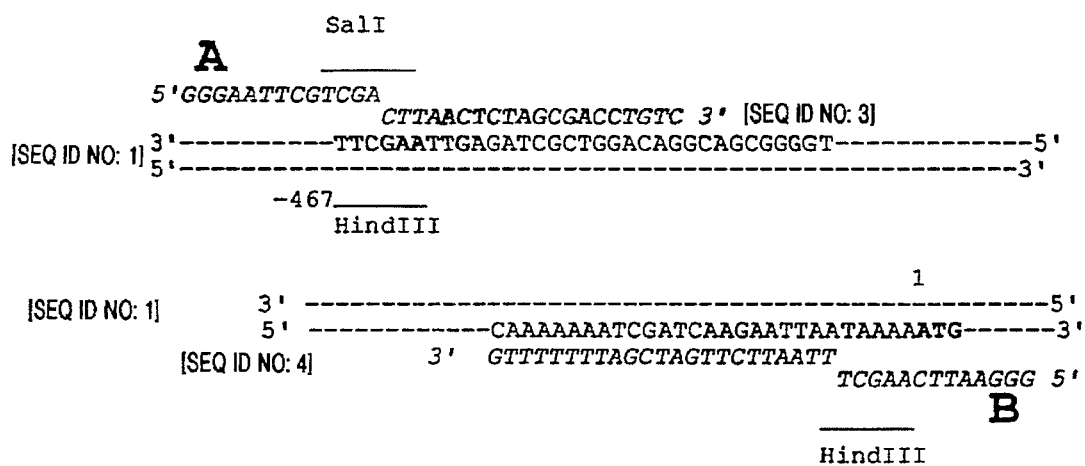
FIG. 5: Sequence and location of the oligodeoxynucleotides used in the PCR reaction for inserting a HindIII site at position −6 with respect to the ATG of the sequence in FIG. 1. The oligodeoxynucleotides are represented in italics [SEQ ID NOS: 3 and 4]. ATG corresponds to the initiation codon for translation of the PGK gene.

A HindIII site was introduced at position −6 relative to the site of initiation of translation (ATG) of the PGK gene using the PCR amplification technique (Mullis et al., Meth. Enzymol. 155:335, 1987), Two oligodeoxynucleotides, which are presented in FIG. 5 [SEQ ID NOS: 3 and 4], were used for this purpose.

The oligodeoxynucleotide A [SEQ ID NO: 3] corresponds to the sequence situated at 467 bp upstream of the ATG codon, at a HindIII site which is replaced by a SalI site during the amplification. The oligodeoxynucleotide B [SEQ ID NO: 4] corresponds to the sequence upstream of the initiation site, and enables a HindIII site to be introduced at position −6.

Figure 8:
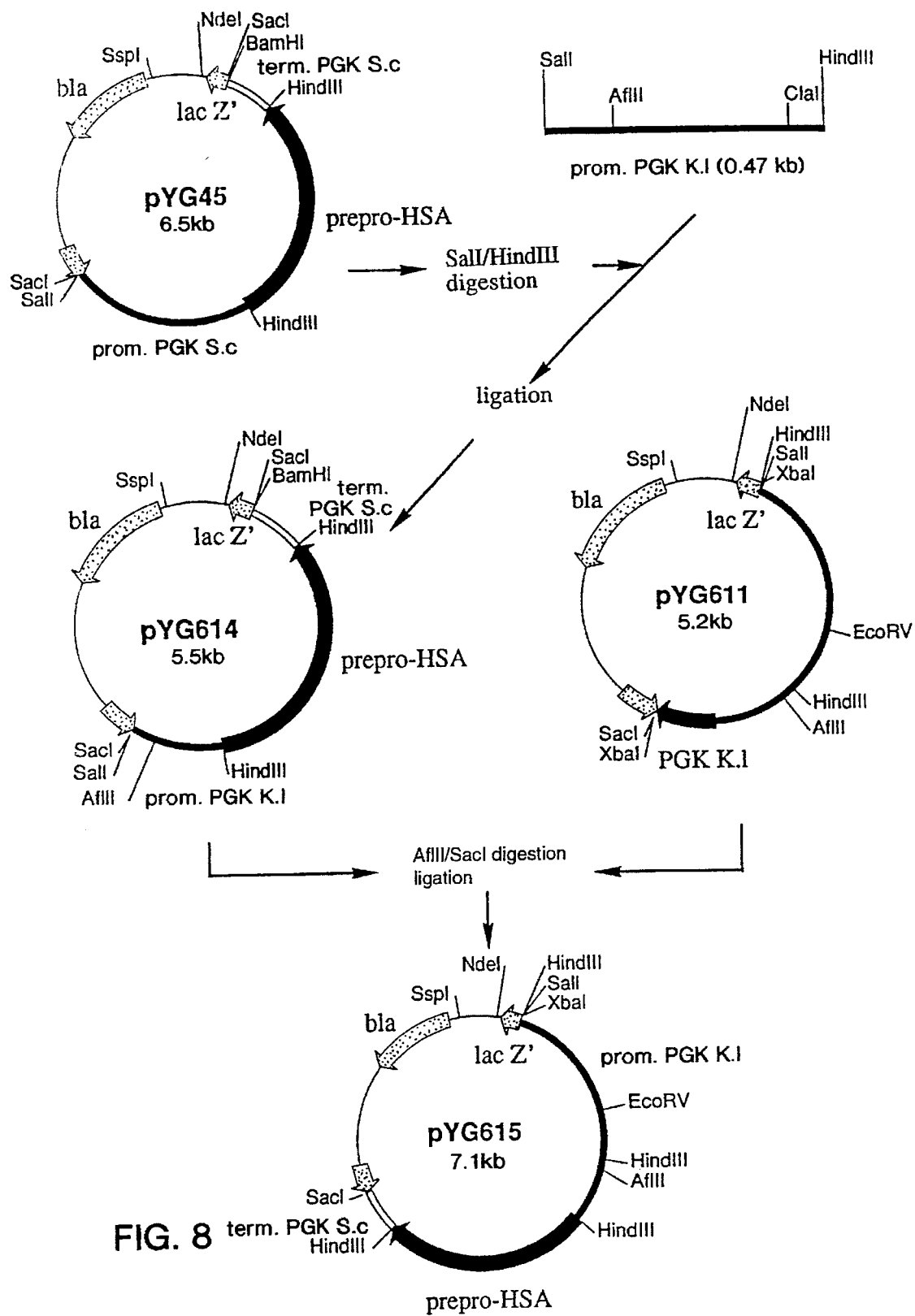
FIG. 8: Strategy for the construction of human serum albumin expression cassettes.

The fragment obtained by PCR was inserted between the SalI and HindIII sites of the bacteriophage M13tg130 in order to verify, by sequencing, that mutations did not occur during the amplification.

b) Construction of human serum albumin expression cassettes: FIG. 8

Figure 7:
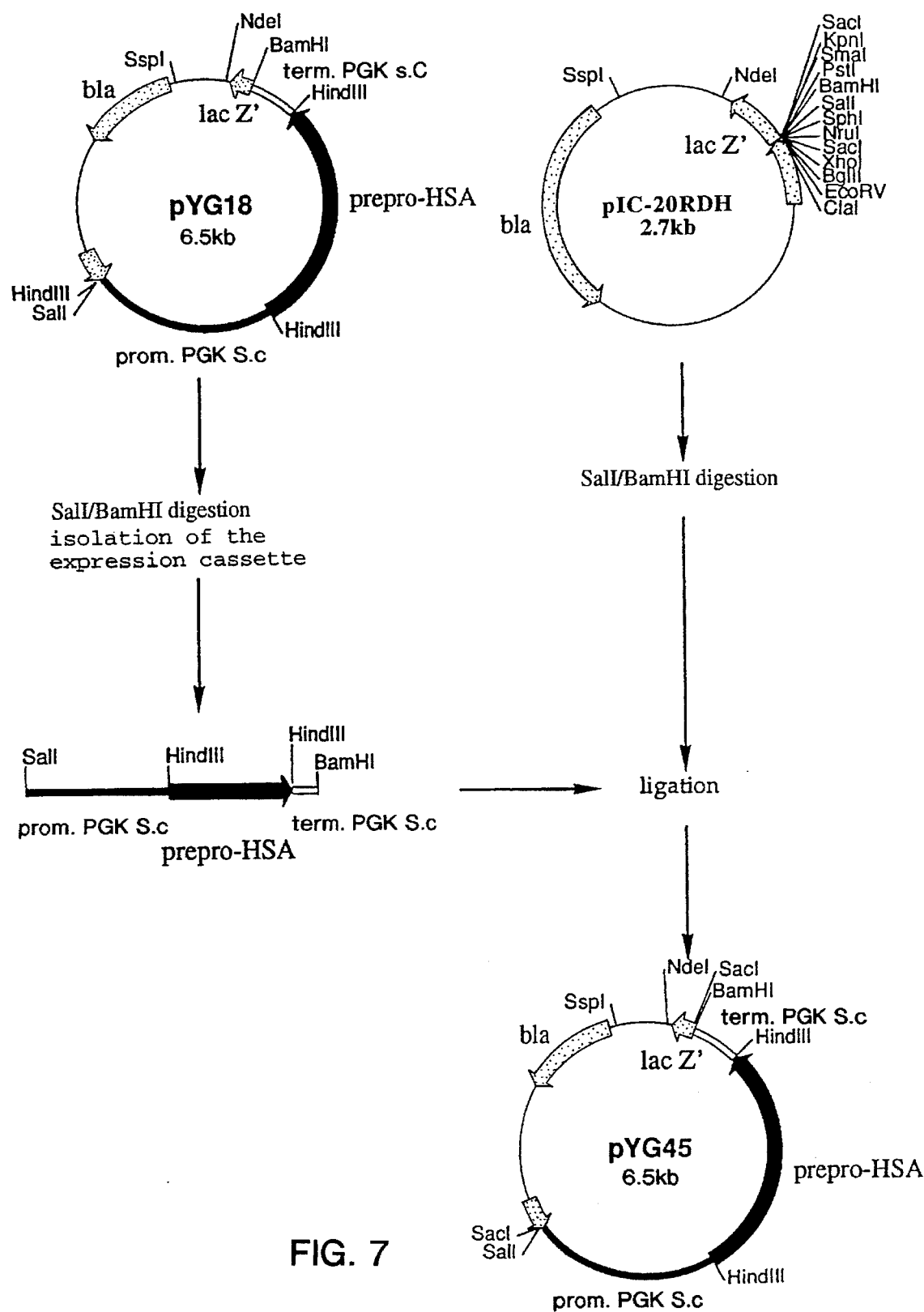
FIG. 7: Strategy for the construction of the plasmid pYG45.

The 474 bp recombinant DNA obtained above was introduced into the SalI and HindIII sites of the plasmid pYG45 (FIG. 7), in order to obtain the vector pYG614 (FIG. 8). The plasmid pYG45 contains an expression cassette consisting of the promoter and the terminator of the *S. cerevisiae* PGK gene between which the prepro-human serum albumin encoding gene (prepro-HSA sequence) is inserted into a HindIII site. pYG45 is derived from pYG18 (see Patent EP 361,991) by subcloning the SalI—BamHI fragment containing the HSA expression cassette into the corresponding sites of the vector pIC-20RDH (FIG. 7). pIC-2ORDH is obtained by digesting the plasmid pIC-20R (March et al., Gene 32:481, 1984) with the enzyme HindIII, filling the ends using the Klenow fragment of *E. Coli* polymerase I and recircularization with T4 DNA ligase.

The SalI—SacI fragment may be isolated from the plasmid pYG614 by digestion. It contains: a promoter region derived from the sequence in FIG. 1, the albumin gene and the terminator of the *S. cerevisiae* PGK gene. It constitutes an expression cassette which may be inserted inside a plasmid so as to constitute an expression vector.

Another expression cassette may be obtained from the plasmid pYG614 by cloning the AflIII—SacI fragment containing part of the PGK promoter of the invention, the albumin gene (prepro-HSA) and the *S. cerevisiae* PGK terminator inside the plasmid pYG611 described above. This generates the plasmid pYG615. The SalI—SacI fragment (containing the complete promoter region of FIG. 1, the prepro-serum albumin-encoding gene, and the terminator of the *S. cerevisiae* PGK gene) may then be isolated by digestion. This fragment constitutes a second albumin expression cassette using the promoter sequence of the invention.

c) Construction of albumin expression vectors

Figure 9:
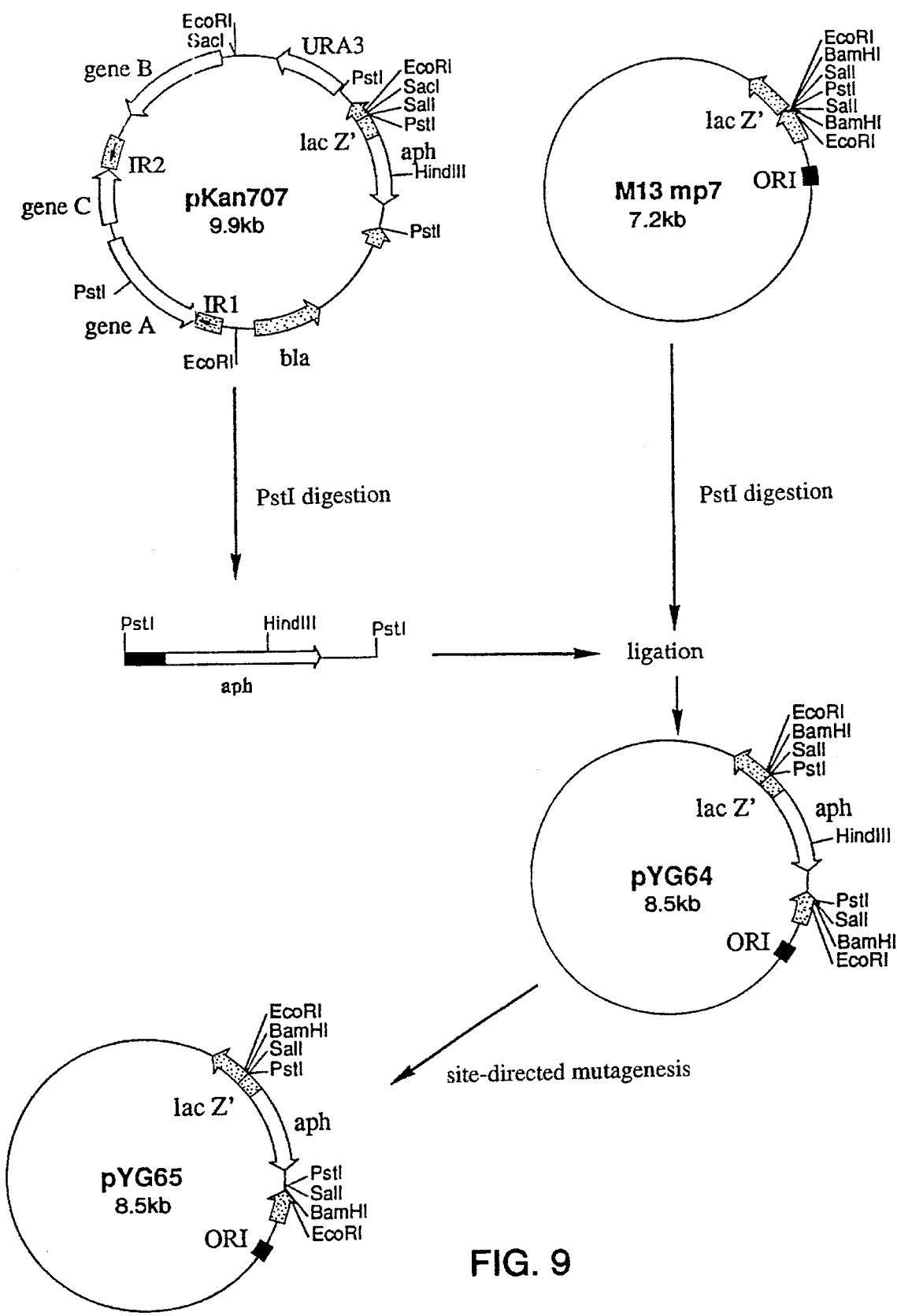
FIG. 9: Strategy for the construction of the plasmid pYG65.
Figure 10:
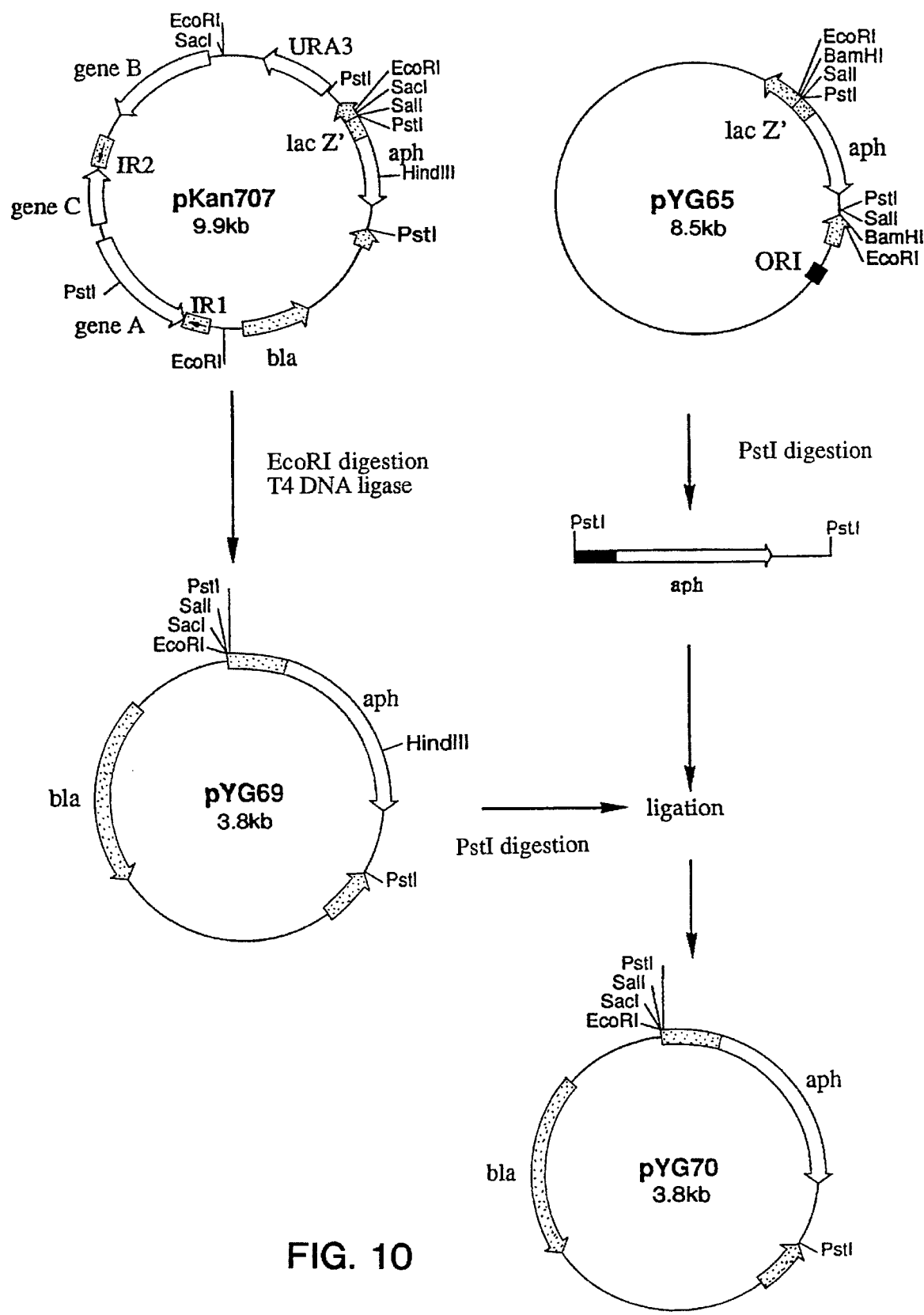
FIG. 10: Strategy for the construction of the plasmid pYG70.
Figure 11:
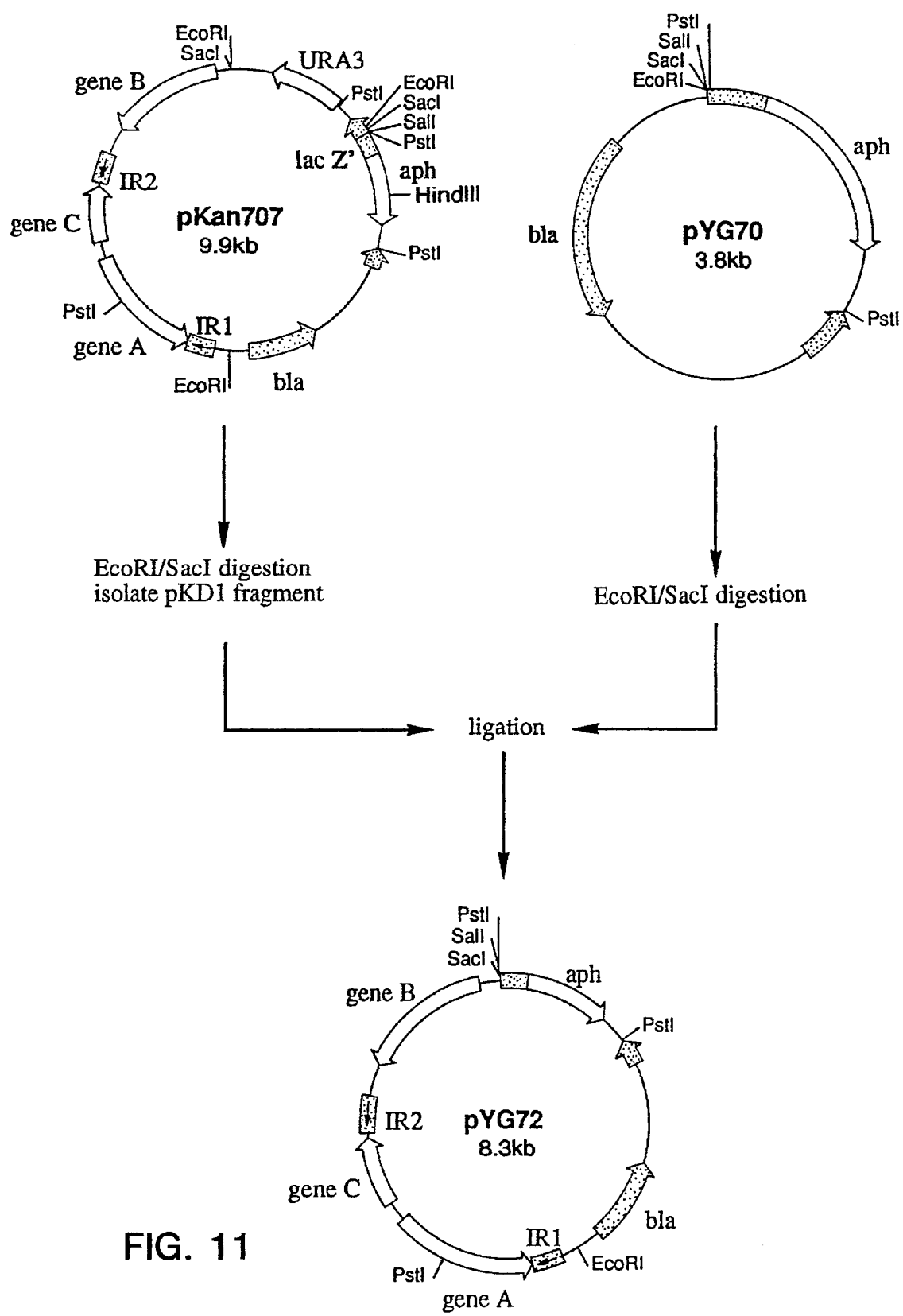
FIG. 11: Strategy for the construction of the plasmid pYG72.
Figure 12:
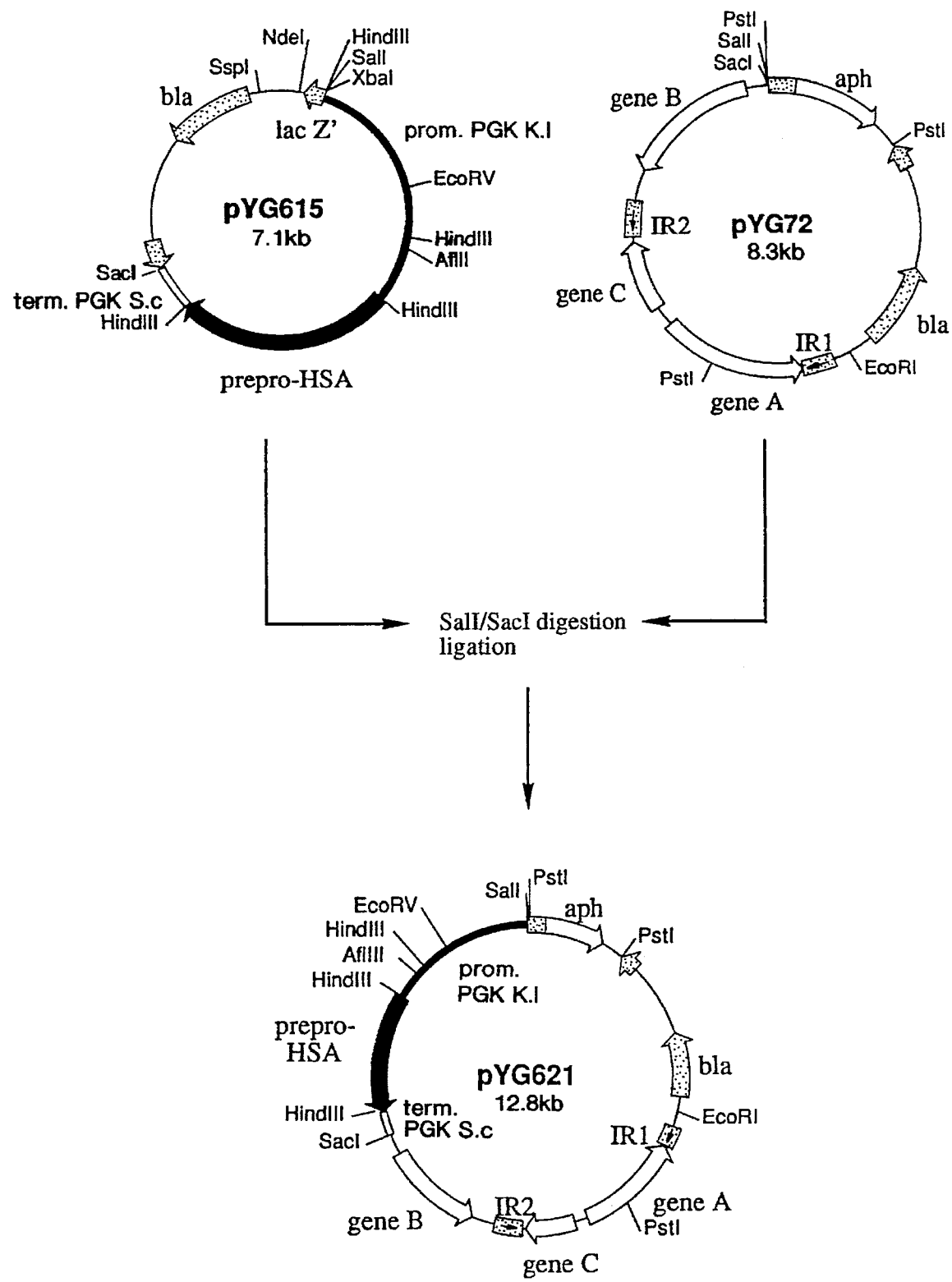
FIG. 12: Strategy for the construction of the vector pYG621.

Albumin expression vectors may be constructed by inserting the expression cassettes obtained above inside *K. lactis*/ *E. coli* shuttle plasmids such as pYG72 (FIG. 10). In particular, an expression vector was obtained (vector pYG621) by inserting the SalI—SacI fragment from pYG615, containing the albumin expression cassette, inside the vector pYG72 (see FIG. 10). This vector corresponds to the plasmid pKan 707 (see EP 361,991 ) from which the SacI fragment, containing the URA3 gene, has been removed, as well as the unique HindIII site present in the aph gene, so as to facilitate subsequent constructions. The aph gene encodes aminoglycoside 3'-phosphotransferase I (Oka et al., J. Mol. Biol. 147:217, 1981) and is used in yeast as a marker for resistance to G418. The PstI fragment of the plasmid pKan 707, containing the aph gene, was subcloned into the bacteriophage M13mp7 to give the vector pYG64 (FIG. 9). The HindIII site present in this gene was destroyed by site-directed mutagenesis according to the method described by Taylor et al., (Nucleic Acid Res. 13:8749, 1985). The resulting plasmid was called pYG65 (FIG. 9). The oligodeoxynucleotide used for the mutagenesis had the sequence 5'-GAA ATG CAT AAG CTC TTG CCA TTC TCA CCG-3'[SEQ ID NO: 9] and transformed the triplet CTT encoding the amino acid 185 (Leu) to CTC. This change does not modify the resulting protein sequence. To construct the plasmid pYG72, the part containing the bacterial replicon of the vector pKan 707 was isolated by digestion with the enzyme EcoRI and recircularization with T4 DNA ligase so as to obtain pYG69. The PstI fragment present in this latter vector, containing the aph gene, was replaced by the equivalent mutant fragment derived from pYG65. This construct was called pYG70. The 4.7 kb pKDI sequence between the EcoRI and SacI sites was introduced inside this latter vector so as to obtain pYG72. The vector pYG621 (FIG. 11) was obtained by insertion of the SalI—SacI fragment containing the albumin expression cassette derived from pYG615.

Example 3

Construction of a Cassette Enabling the Promoter Region to be Used in the 2 Directions This construct was obtained by introducing a SalI site and a HindIII site on either side of the region between the two open reading frames identified in FIG. 2: ORF PGK and ORF X, that is, at nucleotides 1343 and 2246 in FIG. 1.

This construct was produced by the PCR technique using oligodeoxynucleotide A [SEQ ID NO: 5], which introduces a SalI site in the −1 position relative to the site of initiation of translation of the PGK gene, and oligodeoxynucleotide B [SEQ ID NO: 6], which introduces a HindIII site in the −1 position relative to the site of initiation of translation of the X gene (see FIG. 6(a)). Three PCR reactions were carried out using the plasmid pYG610 as the template, so as to remove a HindIII site present in the promoter region:

The first 2 PCRs amplified the regions on either side of the HindIII site using the oligodeoxynucleotides A and B [SEQ ID NOS: 5 and 6] coupled to oligodeoxynucleotides C [SEQ ID NO: 7] and D [SEQ ID NO: 8] respectively (FIG. 6). Oligodeoxynucleotides C and D are complementary and enable a point mutation to be introduced at the level of the inner hindIII site.

The last PCR generated the final fragment, containing the modified promoter region, using the previous 2 amplification products as primer.

This region is then introduced into the vectors described in Example 2, and used as a bi-directional promoter.

Example 4

Expression of Albumin

Figure 13:
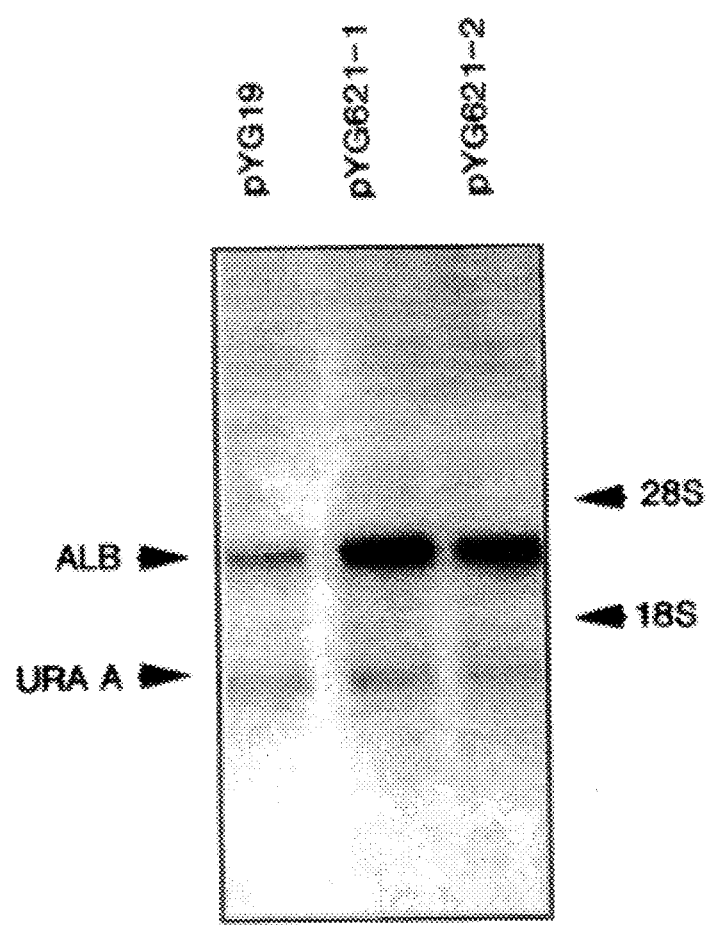
FIG. 13: Visualization, by Northern blotting, of the expression of the human albumin gene under the control of the K. lactis PGK promoter. The samples correspond to 10 μg of total RNA. 18S and 28S are the positions of the 18S and 28S ribosomal RNAs. ALB=fragments recognized by the probe corresponding to the albumin gene; URA= fragments recognized by the probe corresponding to the K. lactis URA A gene serving as loading reference.
Figure 14:
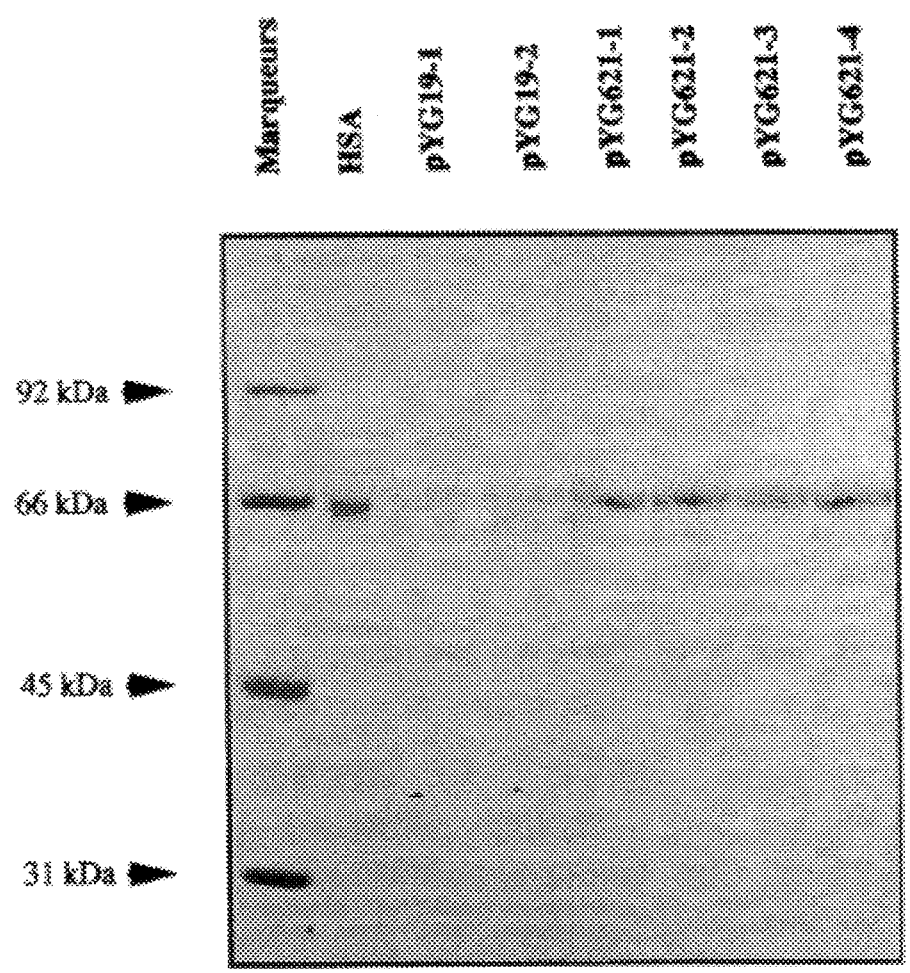
FIG. 14: Visualization of albumin production in strains transformed by the expression vector pYG621 containing the K. lactis PGK promoter. The samples correspond to 30 μl of culture supernatant; the bands at the position of the 66 kd marker correspond to albumin. M=molecular weight markers: bovine carbonic anhydrase (31 kd), ovalbumin (45 kd), BSA (66 kd), rabbit phosphorylase b (92 kd).

The vector pYG621 was introduced, by transformation, into the K. lactis strain MW98-8C (CBS 579.88), using the ethylene glycol/dimethyl sulphoxide technique (Durrens et al. Curr. Genet. 18:7, 1990). This strain is derived from the wild strain CBS2359 and is of the genotype: Mat α, uraA, lysA, argA, R+, cir. The transformant yeast are selected for the G418-resistant phenotype, which the plasmid pYG621 confers, using YPD media (10 g/l yeast extract, 20 g/l peptone, 20 g/l glucose) containing 0.2 g/l of geneticin. Plasmid pYG72-transformed strains not containing an expression cassette were selected to serve as controls in the production tests. Moreover, vector pYG19-transformed strains were also selected in order to compare the efficiency of the K. lactis PGK promoter according to the invention with that from S. cerevisiae. The vector pYG19 is similar to the vector pYG621 except that the albumin gene is under the control of the S. cerevisiae PGK promoter (EP 361,991).
a) Analysis of the mRNAs The cells were cultured at 28° C. in selective YPD media containing 0.2 g/l of geneticin. The total RNAs were extracted (Sherman et al., Methods in Yeast Genetics, Cold Spring Harbor Laboratory, 143, 1986) and separated by electrophoresis on an agarose gel. The RNAs were hybridized to a probe corresponding to the albumin structural gene (1.9 kb HindIII—HindIII fragment) derived from the vector pYG18 (FIG. 7) following the Northern blot method (Maniatis et al., Molecular cloning, Cold Spring Harbor, Laboratory Press, 1982). Autoradiography showed a 2.3 kb band specific to albumin (FIG. 13). Moreover, it is clearly evident that the level of transcription of the albumin gene is substantially higher in the strains containing a promoter region of the invention (pYG621) than in those containing the intact S. cerevisiae PGK promoter (pYG 19).
b) Analysis of the proteins The cells were cultured in Erlenmeyer flasks in selective YPD media containing 0.2 g/l geneticin at 28° C. with shaking. After 96 hours in culture, 30 µl of supernatant were collected and mixed with an equivalent volume of 2×Laemmli buffer (Laemmli, Nature 227:680, 1970). After heating at 96° C. for 10 minutes, the sample proteins were separated on an 8.5% SDS polyacrylamide gel. The production of albumin was then visualized by staining the gel with coomassie blue, and production from the different vectors was compared. FIG. 14 shows that the 4 clones which were obtained separately by transforming the strain MW98-8C using the vector pYG621, secreted substantially more albumin than those obtained by transformation using the vector pYG19.

It is evident that the promoter region of the invention permits excellent albumin production by yeast, greater than that obtained with the S. cerevisiae PGK promoter. This region, or reduced forms or derivatives thereof, constitute(s) an important industrial tool for microbiological, and more particularly eukaryotic, production systems.

One skilled in the art will readily appreciate the present invention is well adapted to carry out the objects and obtain the ends and advantages mentioned, as well as those inherent therein. The DNA sequences, recombinant DNAs, vectors, cells, methods, procedures, and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

Deposit of Strains Useful in Practicing the Invention

Deposits of biologically pure cultures of the following strains were made pursuant to, and in satisfaction of, the Budapest Treaty on the International Recognition of the Deposit of Microorganisms for the Purpose of Patent Procedure, with the American Type Culture Collection, 12301 Parklawn Drive, Rockville, Md. The Accession Numbers indicated were assigned after successful viability testing, and the requisite fees were paid. Access to said cultures will be available during pendency of the patent application to one determined by the Commissioner to be entitled thereto under 37 C.F.R. §1.14 and 35 U.S.C. §122. All restriction on availability of said cultures to the public will be irrevocably removed upon the granting of a patent based upon the application and said cultures will remain permanently available for a term of at least five years after the most recent request for the furnishing of a sample and in any case for a period of at least 30 years after the date of the deposit. Should the cultures become nonviable or be inadvertently destroyed, they will be replaced with viable culture (s) of the same taxonomic description.

| Strain/Plasmid | ATCC No. | Deposit Date |
| --- | --- | --- |

We claim:

1. An isolated and purified DNA sequence selected from the group consisting of:
   (a) the sequence presented in FIG. 1 (SEQ ID NO: 1);
   (b) a derivative of the sequence of (a); and
   (c) a fragment of the sequence of (a);
   wherein said DNA sequence possesses transcriptional promoter activity.

2. A recombinantly prepared DNA comprising a DNA sequence according to claim 1.

3. A recombinantly prepared DNA according to claim 2, further comprising one or more structural genes.

4. A recombinantly prepared DNA according to claim 3, wherein said one or more structural genes is human serum albumin.

5. A recombinantly prepared DNA according to claim 3, further comprising signals permitting the secretion of the expression product of said structural gene(s).

6. A recombinantly prepared DNA according to claim 3, wherein said sequence is a bidirectional promoter and said genes are inserted on each side of the promoter, in the 2 opposite orientations.

7. An autonomous or integrative expression plasmid comprising the recombinantly prepared DNA according to claim 3.

8. A recombinantly prepared cell containing a DNA sequence according to claim 1.

9. The recombinantly prepared cell according to claim 8, characterized in that it is a yeast cell.

10. The recombinantly prepared cell according to claim 9, characterized in that said yeast cell is of the Kluyveromyces genus.

11. A process for the preparation of a recombinant protein by expression of the gene encoding said protein in a cellular host comprising expression of the said gene under the transcriptional control of a sequence according to claim 1.

12. A process according to claim 11, characterized in that the protein is human serum albumin.

13. The process of claim 11, further comprising simultaneous expression of isolated and purified genes, wherein said sequence is a bidirectional promoter and said genes are inserted on each side of the promoter, in the 2 opposite orientations.

14. An isolated and purified DNA sequence according to claim 1, comprising all or part of the sequence presented in FIG. 6(b) (SEQ ID NO: 2).

15. A recombinantly prepared DNA comprising a DNA sequence according to claim 14.

16. A recombinantly prepared DNA according to claim 15, further comprising, one or more structural genes.

17. A recombinantly prepared DNA according to claim 16, further comprising signals permitting the secretion of the expression product of the said structural gene(s).

18. An autonomous or integrative expression plasmid comprising the recombinantly prepared DNA according to claim 16.

19. A recombinantly prepared cell containing a DNA sequence according to claim 14.

20. The recombinantly prepared cell according to claim 19, characterized in that it is a yeast cell.

21. The recombinantly prepared cell according to claim 20, wherein said yeast cell is of the Kluyveromyces genus.

22. A process for the preparation of a recombinant protein comprising expression of the gene encoding said protein in a cellular host wherein the expression of said gene is under the transcriptional control of a sequence according to claim 14.

23. The process of claim 22, further comprising simultaneous expression of isolated and purified genes, wherein said sequence is a bidirectional promoter and said genes are inserted on each side of the promoter, in the 2 opposite orientations.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2250 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Kluyveromyces lactis ( x i ) SEQUENCE DESCRIPTION: SEQ ID NO:1:

```
TCTAGATTTA GCGGGTCATC GAAATTTAGT AGCGAGTCTA TTAGGGACCA GAGTTGCAAC        60
CTGAGGTTTA ATGCGTCATC CTGTCGTTGC TTCAAGTTCC CCACTTGAAT CACTTGGACA       120
AACCGTTTCA TTGGTTTGAG GAAGGTGACG GATCTGGGTA GAAACTGGAC TACTGCATCT       180
GTTGGTAGTC TTGATGCCAT GGTGATGAGC CATTGCCATT GGAAAAGAGT GAATTCAGAT       240
TCCAAGATTT GGTCAATGAT TGATTTGTA  AGATTGAGAT CGTAATCCTG ATACTCTTTG       300
AGCCATGTTT CCAACAGTTC TTCGGAATCT GCCGGTGTGG AAACGAGTAT TTCGGAGTAC       360
AATCTCGGTG GTTGCGTTAT CTGAGAGGAT GGTGTAGTGG TTTGATGTTG CTGTGTGAAA       420
GATGATGCAG AGCTGATCAA CGATTCGAAC TGGGAGATCA CTTCGTTCAC TTCTTCCTGG       480
TTCCCGTTAC CTGTTTGCGT TTCCTCATAC ATTGGTACGC TATCCTCATC TTCAGATAAC       540
GAAATATCAA ACTCATCGGA ATCGGACGCG TCGTTCAAAT CGCCCTCATC CTTGGTAATG       600
TTCTTGAACC GGTCGAGAAG GTTGAGAATC TCTGTCGGAA CACCACCCTG CGGCGTATAC       660
CAGAACCAGA ATAAATTGTA GCACATCTTA ACTTTCTCTA AGGAAACATC TGAACTCTGA       720
TCAACGCATT CCGTAAGTAT ACTGTTTGCC TTGTCTCTGG TGAATTTATG AGGGTAAGAC       780
TCTGAGATCA TAAGTAACTG TTGAGCATCG AAGTTGTTGT AGTTTGAAAT TAGGGATCTG       840
GAAAGATGCG GTACCACTGC TTTGATGACA TTATCTGGCG GGTTCAACGG TACCAATTCC       900
TGCAAGAATA GCGAATCCAA CGGTTTTAAC TCAGAGTAAT GGTTGATCAA CTCGATGAAA       960
ACGTCCCAAT GGATGGATTG CATCAAGTGT TGATGTTCCA CCAAATTAAG ACAATATTTC      1020
GTAACGTTTT CGAGTGAAAC TGACACGGGC CTGCCCTCAG CACTCGTAGA CACGAGTAAC      1080
GTCTTGAGAC CTCTCGTACA GGGAAGCGAC ATATCGTTCA ATAGACTATG AACAAAGTG      1140
TACACCGCAG CGATATCCTT GCATTTGCAA AACGATTGAA TAAGTGACGT CGATGCTAAA      1200
TCCTGGATAA GTACGCTGGT ATCGTGTAAG CCCATGAGAA CGACACGTTC CTCATCACTA      1260
GAAGCCGAAC TGTTGTCTTC AGTGGGGATT GGTTCGACAT TTTGCCAATT GCTGTCGATG      1320
TACCCTTTCA AAGCCATGTA CCTTAAATCT TCATCCTTGG CCAAGTAGAT TCATCGGGTG      1380
TGTTTGAAGT AAGAATATTT GCTTGTTTTT ATGGTATCAA AGGTATATGT TGTAGAAGAC      1440
AATTTCCGGT AATCCAATTG TCTGTCTGCT CAGTTTAGCA CATGTATAGT ACGTTGCACA      1500
TAGTCTACAA TATTCAGCAT TCAGCATTCA GTATACAGCA TATGGCTAAA TGATCACAAA      1560
TGTGATTGAT GATTTGACAC GACTAGAAAA GAGAACGAAA AAGGGAAATT CATGTCACGT      1620
```

-continued

| | | | | | | |
|---|---|---|---|---|---|---|
| GCGTTGGCAC | GTGACATGGA | ATATCGAAGA | AAGAAAAAAA | AAAACGATCT | CGTCCTAGTG | 1680 |
| GAAGCCCAGA | GTCTGGTCCC | CCCGGAGTCT | TCCCAAAACA | AGAAGCTGAC | ACATGTTGAC | 1740 |
| ACAGAACACC | CCACAGCAAA | TGCACCACGC | TACGTAGATC | AGGAAGCTTA | ACTCTAGCGA | 1800 |
| CCTGTCGCTC | GCCCCACAGA | ACCTCACCCG | AGAACCACAC | ATTACGCC | GCCAGCTCCC | 1860 |
| ACTATACTCA | TCTTGCTTCC | CTTAAGCGTT | CTCACGATTC | GTTCGCTGCC | CTTCTTCAAG | 1920 |
| AGTCTTCTGA | TTCTAATTCT | CATTCGAAAT | CCTCTACAGT | TAATGAATTG | CTTGACATGA | 1980 |
| CATTCATTGT | CTCATGGTTT | TGGCTTTTTG | GCTTTGTCT | TTTAAAGCTA | TATCAACTTT | 2040 |
| ACATATAAAT | ATACGTCAAA | AGGGGATTCA | TTAATTAGAA | AATTCTCTTT | TCAATAGTT | 2100 |
| GCTATTCATT | ATCAATCTAT | TCAACTCAAT | TGGTTATTAT | TTTCATCTTT | TTGTCATCCT | 2160 |
| AAACCATCAA | CAATATTTAA | ATATATCTGT | TGCTACATTA | AGAGTTACTT | CAGAAATAAC | 2220 |
| AAAAAAATCG | ATCAAGAATT | AATAAAAATG | | | | 2250 |

(2) INFORMATION FOR SEQ ID NO:2:

(i) SEQUENCE CHARACTERISTICS:
        (A) LENGTH: 917 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Kluyveromyces lactis (xi) SEQUENCE DESCRIPTION: SEQ ID NO:2:

| | | | | | | |
|---|---|---|---|---|---|---|
| AAGCTTTTAA | ATCTTCATCC | TTGGCAAGTA | GATTCATCGG | GTGTGTTTGA | AGTAAGAATA | 60 |
| TTTGCTTGTT | TTTATGGTAT | CAAAGGTATA | TGTTGTAGAA | GACAATTTCC | GGTAATCCAA | 120 |
| TTGTCTGTCT | GCTCAGTTTA | GCACATGTAT | AGTACGTTGC | ACATAGTCTA | CAATATTCAG | 180 |
| CATTCAGCAT | TCAGTATACA | GCATATGGCT | AAATGATCAC | AAATGTGATT | GATGATTTGA | 240 |
| CACGACTAGA | AAAGAGAACG | AAAAGGGAA | ATTCATGTCA | CGTGCGTTGG | CACGTGACAT | 300 |
| GGAATATCGA | AGAAAGAAAA | AAAAAACGA | TCTCGTCCTA | GTGGAAGCCC | AGAGTCTGGT | 360 |
| CCCCCCGGAG | TCTTCCCAAA | ACAAGAAGCT | GACACATGTT | GACACAGAAC | ACCCCACAGC | 420 |
| AAATGCACCA | CGCTACGTAG | ATCAGGAAGC | TTAACTCTAG | CGACCTGTCG | CTCGCCCCAC | 480 |
| AGAACCTCAC | CCGAGAACCA | CACATTACAC | GCCGCCAGCT | CCCACTATAC | TCATCTTGCT | 540 |
| TCCCTTAAGC | GTTCTCACGA | TTCGTTCGCT | GCCCTTCTTC | AAGAGTCTTC | TGATTCTAAT | 600 |
| TCTCATTCGA | AATCCTCTAC | AGTTAATGAA | TTGCTTGACA | TGACATTCAT | TGTCTCATGG | 660 |
| TTTTGGCTTT | TTGGCTTTTG | TCTTTTAAAG | CTATATCAAC | TTTACATATA | AATATACGTC | 720 |
| AAAAGGGGAT | TCATTAATTA | GAAAATTCTC | TTTTCAATA | GTTGCTATTC | ATTATCAATC | 780 |
| TATTCAACTC | AATTGGTTAT | TATTTTCATC | TTTTGTCAT | CCTAAACCAT | CAACAATATT | 840 |
| TAAATATATC | TGTTGCTACA | TTAAGAGTTA | CTTCAGAAAT | AACAAAAAAA | TCGATCAAGA | 900 |
| ATTAATAAAA | AGTCGAC | | | | | 917 |

(2) INFORMATION FOR SEQ ID NO:3:

(i) SEQUENCE CHARACTERISTICS:
        (A) LENGTH: 33 base pairs ( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:3:

GGGAATTCGT CGACTTAACT CTAGCGACCT GTC 33

( 2 ) INFORMATION FOR SEQ ID NO:4:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:4:

GGGAATTCAA GCTTTAATTC TTGATCGATT TTTTTG 36

( 2 ) INFORMATION FOR SEQ ID NO:5:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:5:

CATGTCGACT TTTATTAAT TCTTGATCGA T 31

( 2 ) INFORMATION FOR SEQ ID NO:6:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:6:

ATGAAGCTTA AATCTTCATC CTTGGC 26

( 2 ) INFORMATION FOR SEQ ID NO:7:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:7:

GGGTGAGGTT CTGTGGGGCG AGCGACAGGT CGCTAGAGTT AAGCATCCTG ATC 53

( 2 ) INFORMATION FOR SEQ ID NO:8:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:8:

GATCAGGATG CTTAACTCTA GCGACCTGTC GCTCGCCCCA CAGAACCTCA CCC    53

( 2 ) INFORMATION FOR SEQ ID NO:9:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: other nucleic acid ( x i ) SEQUENCE DESCRIPTION: SEQ ID NO:9:

GAAATGCATA AGCTCTTGCC ATTCTCACCG    30